United States Patent [19]

Goldman

[11] 4,358,288

[45] Nov. 9, 1982

[54] FERTILITY INDICATOR SYSTEM CONTAINING ANTHOCYANIN PIGMENT

[76] Inventor: Dorothee F. E. Goldman, 3503 Shepherd St., Chevy Chase, Md. 20815

[21] Appl. No.: 302,848

[22] Filed: Sep. 16, 1981

[51] Int. Cl.³ .................... G01N 33/52; G01N 33/50
[52] U.S. Cl. .................................. 23/230 B; 23/917; 252/408; 422/61
[58] Field of Search ............... 23/230 B, 917; 422/61; 252/408

[56] References Cited

U.S. PATENT DOCUMENTS

| | | |
|---|---|---|
| 3,271,257 | 9/1966 | Averette . |
| 3,406,016 | 10/1968 | Foster ............................. 23/230 B |
| 3,436,180 | 4/1969 | McSweeney ..................... 23/917 X |
| 3,595,620 | 7/1971 | Gordon ........................... 23/230 B |
| 3,813,222 | 5/1974 | Vietes ............................. 23/230 B |
| 3,968,011 | 7/1976 | Manautou ........................ 435/18 |
| 4,294,922 | 10/1981 | Heap ............................... 23/917 X |

OTHER PUBLICATIONS

Chemical Abstracts, 84:116155t (1976).

*Primary Examiner*—Sidney Marantz
*Attorney, Agent, or Firm*—Gipple & Hale

[57] ABSTRACT

Fertility in females, especially human females, is evaluated by contacting a mucin-containing body fluid such as saliva with a fertility evaluation medium comprising an anthocyanin pigment and a substrate which facilitates generation of a color response in the pigment, in the presence of vaginal fluid or substances similar to those found in the vaginal fluid, especially ascorbic acid and sugars. A resulting color change in the fertility evaluation medium can be used to determine whether the female is not fertile at that time, whether fertility is imminent in the female, or whether the female actually is fertile.

30 Claims, No Drawings

FERTILITY INDICATOR SYSTEM CONTAINING ANTHOCYANIN PIGMENT

The present invention relates to the evaluation of fertility in females, especially human females, and more particularly relates to a system and method for determining, at any time, the stage a woman has reached in her menstrual cycle.

BACKGROUND OF THE INVENTION

It is well-known that the fertility processes which occur in females, especially in human females, are highly complex, and continuing efforts are being made in this area to more fully understand these processes so as to facilitate the development of improved techniques for treating fertility problems as well as more effective and reliable birth control methods. In the fertility problem area, there is an acute need for an improved method of studying women who wish to conceive but are unable to do so, and this need extends to women experiencing other difficulties such as menstrual cycle variations and other problems associated with the female child-bearing organs.

In the birth control area, there is an acute need for improved birth control methods which are not only effective in preventing conception but also have a reduced incidence of adverse physical side effects. There are a wide variety of birth control methods available, but these are often unacceptable due to the fact that they are unreliable (i.e., prevention of conception is not assured), or for medical reasons, or on religious grounds. One example of a birth control method which is unreliable is the so-called "rhythm" method, which is based on the fact that the woman is not fertile, i.e., ovulation has not occurred or is not about to occur, during a certain period in her menstrual cycle. The major disadvantage associated with this method is that, while the time period from when ovulation naturally occurs to the next succeeding menstrual period is essentially fixed in all women, the time period between the beginning of a menstrual period and the next ovulation can vary considerably depending of the particular woman concerned. It is during the time period between the beginning of a menstrual period and the onset of the next succeeding ovulation that sexual intercourse can occcur without conception occurring since during this period the female ovum has not yet been produced by the woman. However, significant risks do exist with the "rhythm" method since, even if the woman has not ovulated at the time of sexual intercourse, ovulation occurring one or two days thereafter can result in conception since the life span of male sperm in the vaginal can be as long as one to two days, and sometimes longer.

Some methods do exist for determining when a woman is about to ovulate but these are inconvenient and difficult to interpret. One such method requires the woman to take her temperature every morning and to plot this on a graph. From the shape of the graph, it is possible to see when ovulation has actually occured, but the major problems associated with this method is that fluctuations in body temperature can occur for many reasons other than the ovulation process.

In view of the above, it can be seen that there exists a need for an improved method for evaluating fertility in woman so that fertility problems can be alleviated and appropriate birth control methods can be selected and reliably practiced, thereby reducing anxiety as well as the risk of unwanted conception.

BRIEF SUMMARY OF THE INVENTION

It has now been found, according to the present invention, that the above-mentioned problems surrounding the determination in woman of the imminency and existence of fertility can be overcome by following a simple and convenient procedure which permits a woman to determine, at any particular time, whether she is not fertile, or whether she is almost fertile or is actually fertile.

According to a first aspect of the present invention, there is provided a method for evaluating fertility in females, especially human females, which method comprises contacting a mucin-containing body fluid of a female, typically saliva, with a fertility evaluation medium comprising an anthocyanin pigment and substrate which facilitates generation of a color response in the pigment, for example a cellulose material, in the presence of vaginal fluid or substances found in vaginal fluid, including ascorbic acid and a sugar selected from one or more of glucose, fructose, sucrose, galactose, sorbose, arabinose, dextrose and the like, and determining from any resulting color change in the fertility evaluation medium whether the female is infertile, or whether fertility in the female is imminent or whether the female is actually fertile at the time the method is performed.

According to another aspect of the present invention, there is provided a fertility evaluation composition comprising an anthocyanin pigment, a substrate for facilitating generation of a color response in the pigment, and vaginal fluid or substances found in vaginal fluid, including ascorbic acid and a sugar, for example, glucose, fructose, sucrose, galactose, sorbose, arabinose, dextrose and the like.

According to a further aspect of the present invention, there is also provided a fertility evaluation kit, comprising a first component including a substrate, for example a cellulose material, typically filter paper, impregnated with an anthocyanin pigment, a second component comprising ascorbic acid, typically in powder form, and a sugar, and a third component comprising a color comparison chart for comparing colors produced on the paper with colors displayed on the chart. The fertility evaluation kit may optionally include written instructions for assisting the user in using the kit and interpreting the results.

The anthocyanins utilized in the fertility evaluation medium of the present invention have the following general formula:

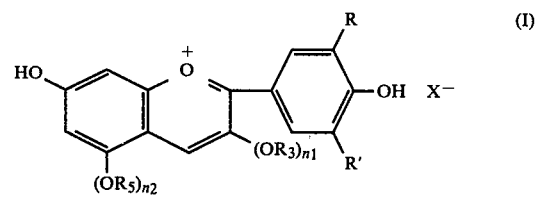

wherein: R is selected from the group consisting of hydrogen, hydroxy, and $C_1$-$C_4$ alkoxy preferably methoxy; R' is selected from the group consisting of hydrogen, hydroxy, and $C_1$-$C_4$ alkoxy, preferably methoxy; $OR_3$ and $OR_5$ are glycosides each selected from the group consisting of glucosides, rutinosides, arabinosides, sophorosides, p-coumaroyl rutinosides, and rhamnosides;

$n_1$ and $n_2$ are each 0 or 1 provided that the sum of $n_1$ and $n_2$ is at least 1; and X' is an anion.

When R is hydroxy and R' is hydrogen, the resulting basic molecule, is, i.e., without the glycoside moieties, is 2-(3,4-dihydroxyphenyl)-3,5,7-trihydroxy-1-benzopyrylium halide, particularly chloride, and is referred to informally as cyanidin chloride. When R and R' are both hydroxy, the resulting basic compound is 3,5,7-trihydroxy-3,4,5-(trihydroxyphenyl)-1-benzopyrylium chloride and is informally referred to as delphinidin chloride. When R' is methoxy and R is hydrogen, the resulting basic compound is 3,5,7-trihydroxy-2-(4-hydroxy-3-methoxyphenyl)-1-benzopyrylium chloride, known informally as peonidin chloride. When R is hydroxy and R' is methoxy, the basic compound is 2-(3,4-dihydroxy-5-methoxyphenyl)-3,5,7-trihydroxy-1-benzopyrylium chloride, referred to informally as petunidin chloride. When R is methoxy and R' is methoxy, the compound is 3,5,7-trihydroxy-2-(4-hydroxy-3,5-dimethoxythenyl)-1-benzopyrylium chloride and is informally referred to as malvidin chloride. When R is hydrogen and R' is hydrogen, the resulting compound is 3,5,7-trihydroxy-2-(4-hydroxyphenyl)-1-benzopyrylium chloride, and is referred to informally as pelargonidin chloride. The 3,5-diglycosides of cyanidin, delphinidin and petunidin are particularly suitable for use in the present invention, as well as the 3-glycoside of delphinidin. It is most preferred, however, to employ, as the anthocyanin pigment, the anthocyanins present in red cabbage leaves. These include cyanidin-3-p-coumaroyl sophoroside-5-glucoside, cyanidin-3-feruloylsophoroside-5-glucoside and cyanidin-3-diferuloylsophoroside-5-glucoside. The manner is which these cyanidin pigments are obtained and utilized in the present invention will be described in more detail hereinbelow.

As will be clear from the more specific description which follows, the present invention enjoys several features and advantages which make it a distinct improvement over prior existing methods for evaluating fertility in women. The major advantage is that the procedure involves visual observation of color changes which occur in the fertility evaluation medium upon contacting that medium with a mucin-containing body fluid of a woman, typically saliva. This procedure can be conducted at any time of the day in contrast to other techniques such as the body temperature method which involves taking the body temperature each morning just after awaking. In contrast, the method of the present invention can be performed when convenient, and the resulting variations in color enable a woman to make a quick and easy determination about her stage of fertility.

A further advantage of the present invention is that it provides a simple and inexpensive diagnostic procedure which can be utilized by obstetricians and gynecologists for conducting initial studies on women suffering from fertility problems. In view of the simplicity of the procedure, it can be conveniently carried out either in the home or in an appropriate treatment center.

A further advantage associated with the present invention is that it can be used by people who wish to control conception, and in some instances may permit these people to selectively use birth control techniques during the fertile period which would not otherwise be available to them for health reasons or other reasons.

Thus, it can be seen that the present invention, by indicating fertility, makes feasible the use of many contraceptive techniques and devices which would otherwise not be possible. In particular, the present invention renders more accurate the "rhythm" method since, as will be discussed in more detail below, the imminency of fertility is indicated by distinct color responses in the fertility evaluation medium.

Another feature of the present invention is that it can be used to study the relationship between fertility and ovulation in the woman and the emotional state of the woman. This may lead to a greater understanding of how variations in the level of hormones may affect moods and feelings. The invention may also be used by women who have reached menopause in order to help them understand how menopause is affecting them physically and emotionally.

Another feature of the present invention is that it can be utilized for evaluating fertility in some female mammals other than women, and also in certain plants. Examples of such applications are in zoological organizations where procreation of certain animal species, especially primates, is critically dependent on the mating time, and also in the agricultural area where the timing of animal mating is important for successful breeding.

DETAILED DESCRIPTION OF THE INVENTION

In the following discussion, for convenience of description, reference will be made to fertility evaluation in human females, although it is to be understood that the present invention has applicability to females in general, and is not limited to use by women.

The fertility evaluation procedure of the present invention involves contacting a mucin-containing body fluid of a woman, physically saliva, with a fertility evaluation medium comprising an anthocyanin pigment of the formula (I) as defined above and a substrate capable of generating a color response in the pigment, typically a cellulose material, and determining from any resulting color change in the fertility evaluation medium whether the woman is not fertile, or whether fertility is imminent or whether she is actually fertile at that time. The fertility evaluation medium should be maintained at temperature not greater than the 180° F., since above 180° F. difficulties arise in discriminating between saliva of a fertile woman and the saliva of a non-fertile woman. It has been observed that the anthocyanin pigment undergoes thermal degradation at temperatures above 190° F., and so the medium must not be permitted to attain temperatures above 180° F. In practice, it is preferred to contact the saliva with the fertility evaluation medium at temperatures of 40° F. to 120° F., more especially 60° F. to 110° F.

As indicated above, the mucin-containing body fluid is typically saliva which, for best results, is preferably freshly produced at the time of conducting each procedure. However, it is not essential for the saliva to be fresh, and it has been found that intelligible results are obtained with saliva which has been frozen for storage purposes. It is preferred to maintain the saliva between room temperature and body temperature during the period that the procedure is being performed.

The sensitivity to color change of the anthocyanin pigment upon contact with the saliva is at its greatest in the pH range of about 4 to 9. In practice, the pH of the fertility evaluation medium should range from about 4.0 to about 6.5.

The fertility evaluation medium of the present invention comprises, in addition to the anthocyanin pigment, a substrate for facilitating the generation of a color response in the pigment when the saliva is brought into contact with the fertility evaluation medium. The substrate is preferably a polysaccharide, and it is especially preferred that this polysaccharide be cellulose obtained from plants or plant products. The polysaccharide chitin may also be utilized, but this is not as preferred as a cellulose substrate. While any cellulose material will generally be satisfactory, it has been found that material such as paper, in particular filter paper, cotton, hemp and particulate cellulose (chromatography grade DEAC) give the best results. Wool materials are not a satisfactory material for use as the substrate in the present invention.

The relative concentrations of the anthocyanin pigment to the substrate material are generally not critical, provided that sufficient substrate material is present to facilitate generation of the desired color response in the fertility evaluation medium. The use of cellulose in different forms as a substrate will be described in more detail below.

In carrying out the method of the present invention, the fertility evaluation medium is contacted with a mucin-containing body fluid, typically saliva, in the presence of vaginal fluid or substances normally found in vaginal fluid, including ascorbic acid and a sugar typically choosen from glucose, fructose, sucrose, galactose, sorbose, arabinose and dextrose. The procedure followed when the substrate is a paper product is not the same as when the method is carried out utilizing a solution of the pigment, and the differences in the procedure adopted will be described in more detail below.

Generally, the ascorbic acid is present in a concentration of from about 0.1 to 10% by weight, preferably from about 0.5 to 5% by weight, and especially about 1% by weight. The concentration of the sugar is generally from about 0.5 to 2% by weight, preferably from about 0.5 to 1.5% by weight, especially about 1%. Optimum results occur when the concentration of both the ascorbic acid and the sugar in aqueous solution is in the region of about 1% by weight. When the substrate is paper, typically filter paper (e.g., about six centimeters in diameter), it is preferably impregnated with an anthocyanin pigment solution wherein the concentration of the pigment ranges from 0.01 mg/ml to 1 mg/ml depending on the particular anthocyanin pigment employed. For cyanidin, the concentration is of the order of 1 mg/ml, whereas when the anthocyanin is delphinidin, the concentration is of the order of 0.01 mg/ml. When the anthocyanin is petunidin, the concentration is of the order of 0.1 mg/ml.

When the method of the invention is carried out utilizing a cellulose substrate, typically a paper substrate such as paper towel or filter paper, intelligible results are not obtained using pure ascorbic acid, and it has been found necessary to utilize a natural fruit source of ascorbic acid such as lemon juice, tomatoes, oranges and the like. Thus, when using this type of substrate, according to one approach an aqueous solution of the anthocyanin pigment, e.g., 1 mg/ml of cyanidin pigment, is applied to the paper so that the paper becomes completely impregnated with the pigment. The impregnated paper is then dried under ambient conditions, and can subsequently be stored in a cool, dry dark place for a period which can be six months and can be as long as two years. In an alternative and preferred way of preparing the substrate, red cabbage leaves are ground, e.g., in a food processor, and then contacted with the cellulose substrate, usually by pressing between paper towels, filter paper, cotton, or the like, so that the pigment is impregnated into the substrate. The pigments contained in red cabbage include cyanidin-3-p-coumaroylsophoroside-5-glucoside, cyanidin-3-feruloylsophoroside-5-glucoside and cyanidin-3-diferuloylsophoroside-5-glucoside, and the substrate impregnated with these cyanidin pigments gives particularly good results in the method of the invention. It is important that the grinding procedure be conducted utilizing non-ferrous equipment in order to avoid chelating problems with the pigments, and it is preferred to utilize stainless steel or plastic grinding apparatus.

In use, the paper substrate impregnated as described above with anthocyanin pigment is contacted either with vaginal fluid, or with a natural fruit source of ascorbic acid, typically lemon juice, tomato juice, orange juice or the like, and a sugar, and the woman then applies freshly produced saliva directly onto the substrate, e.g., by spitting onto the substrate. As indicated above, intelligible results are not obtained when pure ascorbic acid is utilized with a paper or cotton substrate, and is is necessary to employ a natural fruit source of ascorbic acid in order to obtain proper color responses in the fertility evaluation medium.

The resulting color image, if any, will depend on whether the woman is not yet fertile, or whether the woman is about to become fertile or whether the woman is actually fertile at the time of conducting the procedure. The appearance of a blue or darker color of any intensity in the filter paper indicates that the woman is not fertile that time. For example, when cyanidin anthocyanins are employed as the pigment, it has been found that, in a thirty-one day cycle from the onset of menstruation (day one) to about day twelve, the color resulting from the presence of non-fertile saliva can vary from blue to grey to purple.

The appearance of a bright pink color with separate blue spots indicates that fertility is imminent. This reaction occurs six to zero days prior to the actual time when conception can be achieved. Within hours after ovulation has actually occurred, the resulting color is blue. About seven to nine days after the peak of the fertility period, a second phase of blue with pink spots is observed and this phase lasts anywhere from one to two days thereafter.

The appearance of a bright pink color with white spots with the complete absence of blue color means that the woman is fertile at the time the saliva is applied to the fertility evaluation medium. This color reaction appears over a period of about twelve to thirty-six hours, depending on the actual length of the time over which to woman is fertile.

When the substrate is cellulose in powder form, the following procedure may be adopted. 1 ml of a solution of about 1 mg/ml of cyanidin pigment is mixed with about 8 ml of saliva and to this is added about 1 ml of a solution containing about 1 to 10% by weight, preferably about 1% by weight, ascorbic acid, and about 1% by weight of a sugar, usually dextrose or sucrose. Alternatively, vaginal fluid may be added to the solution of the pigment. To the resulting solution is added powdered cellulose, and the particulate size of the cellulose is not critical except that the particles should be sufficiently large in order to permit easy observation of any color change occurring in the presence of saliva. It is to be noted that with this mode of operation utilizing particulate cellulose in an aqueous environment, intelligible results are obtained utilizing laboratory grade ascorbic acid, and it is not necessary to employ a natural fruit source of ascorbic acid (although this could be employed if desired). This is to be contrasted with the situation earlier described when the substrate is a paper or cotton or hemp substrate where a natural fruit source of ascorbic acid must be used. The following color reactions may be observed depending on the woman's state of fertility at the time of the test. When the woman is infertile, large clumps form about the cellulose which gradually turn blue in color. The background solution is purple or dark pink or white/purple in color, and the clumps which form in the medium can be manually removed without losing their blue color. Upon removal from the medium, these clumps gradually turn brown as they dry. If the test is conducted about five to six days prior to the onset of fertility, the result is the appearance of follicular precipitations which mix more readily with the medium, and are difficult to remove manually from the medium. This is in contrast to the formation of large clumps which, as described above, are formed when the woman is in an infertile stage. The background solution is a bright pink color, and the color of the follicular precipitations varies from blue to lavendar depending on how close the woman is to actually becoming fertile.

When the woman is actually fertile, the follicular precipitates (this may appear as a suspension in the medium) are white in color with a pale pink background, and are formed over a period of about twelve to thirty-six hours, sometimes only twelve to eighteen hours. The suspension material can be removed from the solution by evaporation, and is more resistant to oxidation than the large clumps of material which are formed when the test is conducted during an infertile period.

When the woman is in a post-fertile period, a reaction is observed in the medium which is similar to that observed in the infertile period, namely, large clumps are formed which gradually turn blue in color. However, about one week after the fertile stage, the formation of a second slightly follicular suspension occurs which is somewhat more pink from the other reactions described above and lasts about one or two days.

When the woman is at the stage just prior to menstruation, the clumping becomes more and more definite, and the color of the clumps shifts from blue towards purple/grey.

From the above discussion, it can be seen that there is a significant and easily discernible change in the nature of the reaction products and the resulting reaction color when fertility is about five or six days away. With this information, it is possible to more accurately practice the "rhythm" method since the appropriate change in reaction color indicates that fertility is five or six days away and that consequently the risk of conception is substantially increased if sexual intercourse is engaged in during that period.

I claim:
1. Method for evaluating fertility in females, said method comprising:
  (a) providing a fertility evaluation medium comprising an anthocyanin pigment and a substrate for facilitating the generation of a color response in the pigment;
  (b) contacting a mucin-containing body fluid of a female with said fertility evaluation medium in the presence of vaginal fluid or substances found in vaginal fluid, including ascorbic acid and a sugar; and
  (c) determining from a resulting color change in said fertility evaluation medium whether said female is infertile, or whether fertility in said female is imminent, or whether said female is actually fertile.

2. Method according to claim 1, wherein said anthocyanin pigment is of the general formula:

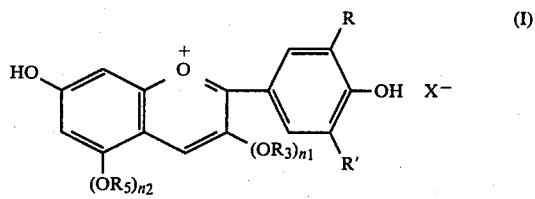

wherein R is selected from the group consisting of hydrogen, hydroxy, and $C_1$-$C_4$ alkoxy; R' is selected from the group consisting of hydrogen, hydroxy, and $C_1$-$C_4$ alkoxy; $OR_3$ and $OR_5$ are glycosides selected from the group consisting of glucosides, rutinosides, arabinosides, sophorosides, p-coumaroyl rutinosides and rhamnosides; $n_1$ and $n_2$ are each 0 or 1, provided that the sum of $n_1$ and $n_2$ is at least 1, and X' is an anion.

3. Method according to claim 1 wherein said mucin-containing body fluid is contacted with said fertility evaluation medium at a temperature of from 40° F. to 99° F.

4. Method according to claim 3 wherein said temperature is 40° F. to 90° F.

5. Method according to claim 1 wherein said fertility evaluation medium is maintained at pH of from 4 to 9.

6. Method according to claim 5 wherein said pH is 4.0 to 6.5.

7. Method according to claim 1 wherein said mucin-containing body fluid is saliva.

8. Method according to claim 1 wherein said substrate is a cellulose material selected from the group consisting of paper, cotton, hemp and powdered cellulose.

9. Method according to claim 1 wherein the female is a human female.

10. Method according to claim 1 wherein said sugar is selected from the group consisting of glucose, fructose, sucrose, galactose, sorbose, arabinose and dextrose.

11. Method according to claim 1 wherein said ascorbic acid is present in a concentration of from about 0.1 to 10% by weight.

12. Method according to claim 1 wherein said sugar is present in a concentration of about 1% by weight.

13. Method according to claim 1 wherein said anthocyanin pigment is derived from red cabbage, and includes cyanidin-3-p-coumaroyl sophoroside-5-glucoside, cyanidin-3-feruloylsophoroside-5-glucoside and cyanidin-3-diferuloylsophoroside-5-glucoside.

14. Method according to claim 1 wherein said anthocyanin pigment is cyanidin-3,5-diglucoside.

15. Method according to claim 1 wherein said anthocyanin pigment is delphinidin-3-glucoside.

16. Method according to claim 1 wherein said fertility evaluation medium comprises filter paper which has been impregnated with an anthocyanin pigment by applying to said filter paper a aqueous solution of said anthocyanin pigment in which said anthocyanin pigment is present in a concentration of from about 0.01 mg/ml to about 1 mg/ml.

17. Method according to claim 16 wherein said anthocyanin pigment is cyanidin, and the concentration of said aqueous solution is about 1 mg/ml.

18. Method according to claim 16 wherein said anthocyanin pigment is delphinidin and the concentration of said aqueous solution is about 0.01 mg/ml.

19. Method according to claim 16 wherein said anthocyanin pigment is petunidin, and the concentration of said aqueous solution is about 0.1 mg/ml.

20. Method according to claim 1 wherein said fertility evaluation medium comprises paper which has been impregnated with anthocyanin pigments present in red cabbage.

21. Method according to claim 1 wherein said substrate is selected from paper, cotton, and hemp, and said substrate is contacted with natural fruit source of ascorbic acid.

22. Method according to claim 21 wherein said natural fruit source of ascorbic acid is selected from the group consisting of lemon juice, tomato juice, and orange juice.

23. A composition suitable for use in evaluating fertility in females, said composition comprising an anthocyanin pigment, a substrate for facilitating generation of a color response in said pigment, and vaginal fluid or substances found in vaginal fluid, including ascorbic acid and a sugar.

24. A composition according to claim 23 wherein said sugar is selected from the group consisting glucose, fructose, sucrose, galactose, sorbose, arabinose and dextrose.

25. A composition according to claim 23 wherein said substrate is a cellulose material selected from the group consisting of paper, cotton, hemp and powdered cellulose.

26. A composition according to claim 25 wherein said anthocyanin pigment is present in an amount of from about 0.01 mg/ml to about 1 mg/ml, and said cellulose substrate is present in an amount of about 10% by weight.

27. A composition according to claim 23 wherein said ascorbic acid is present in an amount of about 1% by weight and said sugar is present in an amount of about 1% by weight.

28. A composition according to claim 25 wherein said cellulose material is filter paper which has been impregnated with said anthocyanin pigment.

29. A composition according to claim 28 wherein said ascorbic acid is present in a natural fruit source of ascorbic acid.

30. A fertility evaluation kit suitable for use in the evaluation of fertility in females, said kit including a first, second and third component, said first component comprising an anthocyanin pigment and a substrate for facilitating the generation of a color response in said pigment, said second component comprising ascorbic acid and a sugar selected from the group consisting of glucose, fructose, sucrose, galactose, sorbose, arabinose and dextrose, said third component comprising a color comparison chart for comparing colors produced on said substrate with color displayed on the chart.

* * * * *